US006102860A

United States Patent [19]
Mooney

[11] Patent Number: 6,102,860
[45] Date of Patent: Aug. 15, 2000

[54] ULTRASOUND TRANSDUCER FOR THREE-DIMENSIONAL IMAGING

[75] Inventor: Matthew Mooney, Westford, Mass.

[73] Assignee: Agilent Technologies, Inc., Palo Alto, Calif.

[21] Appl. No.: 09/220,397

[22] Filed: Dec. 24, 1998

[51] Int. Cl.[7] ........................................ A61B 8/00
[52] U.S. Cl. .................... 600/443; 600/459; 128/916
[58] Field of Search ................... 600/459, 443, 600/447; 128/916; 310/334, 336

[56] References Cited

U.S. PATENT DOCUMENTS

| | | | |
|---|---|---|---|
| 4,277,712 | 7/1981 | Hanafy | 310/334 |
| 4,564,980 | 1/1986 | Diepers | 310/334 |
| 4,641,660 | 2/1987 | Bele | 600/459 |
| 4,694,434 | 9/1987 | Von Ramm et al. | 128/916 |
| 5,027,820 | 7/1991 | Pesque | 128/660.07 |
| 5,103,129 | 4/1992 | Slayton et al. | 600/459 |
| 5,229,933 | 7/1993 | Larson, III | 364/413.25 |
| 5,267,221 | 11/1993 | Miller et al. | 367/140 |
| 5,329,498 | 7/1994 | Greenstein | 367/155 |
| 5,435,313 | 7/1995 | Noda et al. | 128/662.03 |
| 5,460,181 | 10/1995 | Seyed-Bolorforosh | 128/661.01 |
| 5,462,057 | 10/1995 | Hunt et al. | |
| 5,573,001 | 11/1996 | Petrofsky et al. | 128/661.01 |
| 5,575,290 | 11/1996 | Teo et al. | 128/661 |
| 5,590,658 | 1/1997 | Chiange et al. | 128/661.01 |
| 5,622,177 | 4/1997 | Breimesser et al. | 128/662.06 |
| 5,655,536 | 8/1997 | Takamizawa | 128/661.01 |
| 5,671,746 | 9/1997 | Dreschel et al. | 128/661.01 |
| 5,690,114 | 11/1997 | Chiange et al. | 128/661.01 |
| 5,732,706 | 3/1998 | White et al. | 128/661.01 |
| 5,744,898 | 4/1998 | Smith et al. | 310/334 |
| 5,797,845 | 8/1998 | Barabash et al. | 600/443 |
| 5,897,501 | 4/1999 | Wildes et al. | 600/444 X |
| 6,014,897 | 1/2000 | Mo | 73/628 |

OTHER PUBLICATIONS

T. Ota, "Accuracy of Left Ventricular Stroke Volume Measurement Using Real–Time, Three Dimensional Echocardiography Flow Probe in Vivo", 70th Scientific Session Amer. Heart Assn. Meeting, Nov. 11, 1997.

Goldberg, Ri.L. et al, "Multilayer Piezoelectric Ceramics for Two–Dimensional Array Transducers", IEEE Transactions on Ultrasonics, Ferroelectrics & Freq. Control, vol. 41, No. 5, Sep. 1994, pp. 761–771.

Takahiro Ota et al, Novel Determination of Left Ventricular, vol. by Tracing Arbitrary Planes Using Real–Time, 3D Echocardiography: In Vitro and In Vivo Validation, 709th Scientific Session American Heart Assn. Meeting, Nov. 11, 1997, p. 1832.

Fleishman, C. E. et al, "Evaluation of Atrioventricular Valve Abnomarlities Using Real–Time Three Dimensional Echocardiography", 70th Scientific Session Amer. Heart Assn. Meeting, Nov. 11, 1997, p. 1045.

Ming Shu et al, "Tricuspid Velocity Profiles Reflect Right Ventricular Diastolic Wall Motion Abnormalities: Real–Time 3D Echocardiography and Computational Fluid Dynamics", 70th Scientific Session Amer. Heart Assn. Meeting, Nov. 11, 1997, p. 2990.

Takahiro S. et al, "Application of a New Real–Time Three–Dimensional Method for Evaluating Right Ventricular Stroke Volume", 70th Scientific Session Amer. Heart Assn. Meeting, Nov. 11, 1997, p. 1830.

(List continued on next page.)

Primary Examiner—Francis J. Jaworski

[57] ABSTRACT

An ultrasound transducer assembly for use in a phased array ultrasound imaging system includes an array of ultrasound transducer elements having a two-dimensional transmitting and receiving surface that is curved in at least two orthogonal directions and conductors for connecting the transducer elements to electronic circuitry of the ultrasound imaging system. The array may include a curved, two-dimensional array of rows and columns of transducer elements. The transmitting and receiving surface is typically convex but may also be concave. The transmitting and receiving surface may be a portion of a spheroid or an ellipsoid. In one embodiment, the transmitting and receiving surface is configured as a portion of a spherical surface.

25 Claims, 6 Drawing Sheets

OTHER PUBLICATIONS

S. Smith et al, "Two–Dimensional Array Transducers Using Hybrid Connection Technology", IEEE, Oct. 1992, pp. 555–558, vol. 1.

L. Daane et al, "A demountable Interconnect System for a 50x50 Ultrasonic Imaging Transducer Array", IEEE, Sep. 1997, pp. 978–982.

S. Smith et al, "2–D Array Transducers for Medical Ultrasound at Duke University: 1996", ISAF '96 Proceedings of the 10th IEEE Int'l. Symposium on Appl. of Ferroelectrics, vol. 1, Aug. 1996, pp. 5–11.

R. Goldberg et al, "Multilayer 2–D Array Transducers with Integrated Circuit Transmitters and Receivers: A Feasibility Study", IEEE, 1994 Ultrasonics Symposium, pp. 1511–1514.

A. L. Robinson et al, "Applications of Microelectronics and Microfabrication to Ultrasound Imaging Systems", IEEE 1992, Ultrasonics Symposium Proceedings, vol. 1, pp. 681–691.

ULTRASOUND TRANSDUCER FOR THREE-DIMENSIONAL IMAGING

FIELD OF THE INVENTION

This invention relates to medical ultrasound imaging and, more particularly, to ultrasound transducer assemblies that may be used for three-dimensional ultrasound imaging.

BACKGROUND OF THE INVENTION

Medical ultrasound imaging systems typically use a one-dimensional phased array to form an image of a two-dimensional slice through a patient's body. This approach has limitations. First, the two-dimensional slice is always perpendicular to the face of the transducer, thereby limiting the choice of views. For example, a cardiologist sometimes wants to view heart valves in plane. This requires a double oblique imaging plane with respect to the face of the transducer. This plane can only be derived from three-dimensional data. Second, anatomy such as the left ventricle is inherently three-dimensional. To obtain an accurate volume measurement of the left ventricle, three-dimensional data must be acquired.

Current methods used to acquire three-dimensional data, such as maybe obtained using Hewlett-Packard's Omni Plane transducers, use a one-dimensional array that is mechanically moved in a second dimension. This method may require several minutes to obtain a three-dimensional data set. Furthermore, the organs of interest may move during acquisition of the three-dimensional data set.

Phased array ultrasound transducers having multiple elements in the azimuth direction and a few elements in the elevation direction permit scanning in the azimuth direction and elevation focusing. See for example, U.S. Pat. No. 5,462,057 issued Oct. 31, 1995 to Hunt et al. These transducer configurations, often referred to as 1.5 dimensional arrays, do not permit beam steering in the elevation direction.

Planar, two-dimensional transducer arrays may be used for three-dimensional ultrasound imaging. However, in order to obtain good resolution and large steering angle, a large number of extremely small transducer elements is required. Such transducer arrays are difficult to fabricate and are difficult to interconnect to the imaging system electronics.

A system capable of acquiring real-time, three-dimensional data by electronically steering in two dimensions is described by T. Ota in "Accuracy of Left Ventricular Stroke Volume Measurement Using Real-Time, Three Dimensional Echocardiography Flow Probe in Vivo", 70th Scientific Session American Heart Association Meeting, Nov. 11, 1997. This system uses 512 active transducer elements. Signals from the transducer elements are passed through a cable having 512 coaxial conductors into a system with appropriate electronics. The image quality of the system is limited due to the small number of transducer elements used. Furthermore, since the cable between the transducer and the system has a significant diameter, it is difficult to extend this technology to many more transducer elements without an unacceptably large cable or a cable with such small diameter conductors that significant signal loss will occur.

Curved linear transducer arrays have been used for two-dimensional ultrasound imaging. The array has a radius of curvature, so that the individual transducer elements point in different directions. Thus, scanning can be achieved with little or no beam steering on transmit. Furthermore, the same field of view and resolution can be obtained with fewer and larger elements than a flat array.

A device for three-dimensional focusing of an ultrasonic beam is disclosed in U.S. Pat. No. 5,027,820, issued Jul. 2, 1991, to Pesque. The device includes a cylindrical phased array. An acoustic beam may be created by phasing the elements of a selected circumferential segment along the length of the cylindrical array. Although the element count is reduced in comparison with a planar array, the sampling in the circumferential direction is much coarser than the sampling in the lateral direction and provides an irregular data set. A drawback of the cylindrical array is that a large number of elements is still needed along the length of the transducer to achieve an acceptable field of view.

None of the known prior art ultrasound imaging techniques have achieved high quality, high resolution, three-dimensional ultrasound imaging with transducer assemblies that are practical in size, cost and complexity.

SUMMARY OF THE INVENTION

According to a first aspect of the invention, an ultrasound transducer assembly is provided for use in a phased array ultrasound imaging system. The transducer assembly comprises an array of ultrasound transducer elements having a two-dimensional transmitting and receiving surface that is curved in at least two orthogonal directions and conductors for connecting the transducer elements to the ultrasound imaging system. The array may comprise a curved, two-dimensional array of rows and columns of transducer elements, or of transducer elements uniformly or non-uniformly distributed over the transmitting and receiving surface.

The transmitting and receiving surface is preferably convex but may also be concave. The transmitting and receiving surface may comprise a portion of a spheroid or an ellipsoid. In one embodiment, the transmitting and receiving surface comprises a portion of a spherical surface.

According to another aspect of the invention, a phased array ultrasound imaging system is provided. The system comprises an array of ultrasound transducer elements having a two-dimensional transmitting and receiving surface that is curved in at least two orthogonal directions, a transmit beamformer and a receive beamformer each coupled to the transducer array, and a display assembly. The transmit beamformer controls transmission of ultrasound energy with the transducer array into a region of interest in a patient's body. The receive beamformer processes received signals representative of received ultrasound echoes to form at least one receive beam and to generate image data representative of the ultrasound echoes in the receive beam. The display assembly displays an ultrasound image of the region of interest in response to the image data.

The transmit beamformer may comprise means for transmitting ultrasound energy with different active apertures on the array, and the receive beamformer may comprise means for forming receive beams and generating image data corresponding to each of the active apertures, wherein the image data represents a three-dimensional image volume.

According to another aspect of the invention, an ultrasound transducer assembly is provided for use in a phased array ultrasound imaging system. The transducer assembly comprises a transducer handle containing an array of ultrasound transducer elements having a two-dimensional transmitting and receiving surface that is curved in at least two orthogonal directions, a transducer connector for connecting the transducer assembly to an electronics unit of the ultrasound imaging system, and a transducer cable interconnecting the handle and the connector. The transducer cable includes conductors for connecting the array to the electronics unit of the ultrasound imaging system. The transducer handle may include switching circuitry and/or other electronics to reduce the required number of conductors in the transducer cable.

BRIEF DESCRIPTION OF THE DRAWINGS

For a better understanding of the present invention, reference is made to the accompanying drawings, which are incorporated herein by reference and in which.

DETAILED DESCRIPTION

Figure 1:
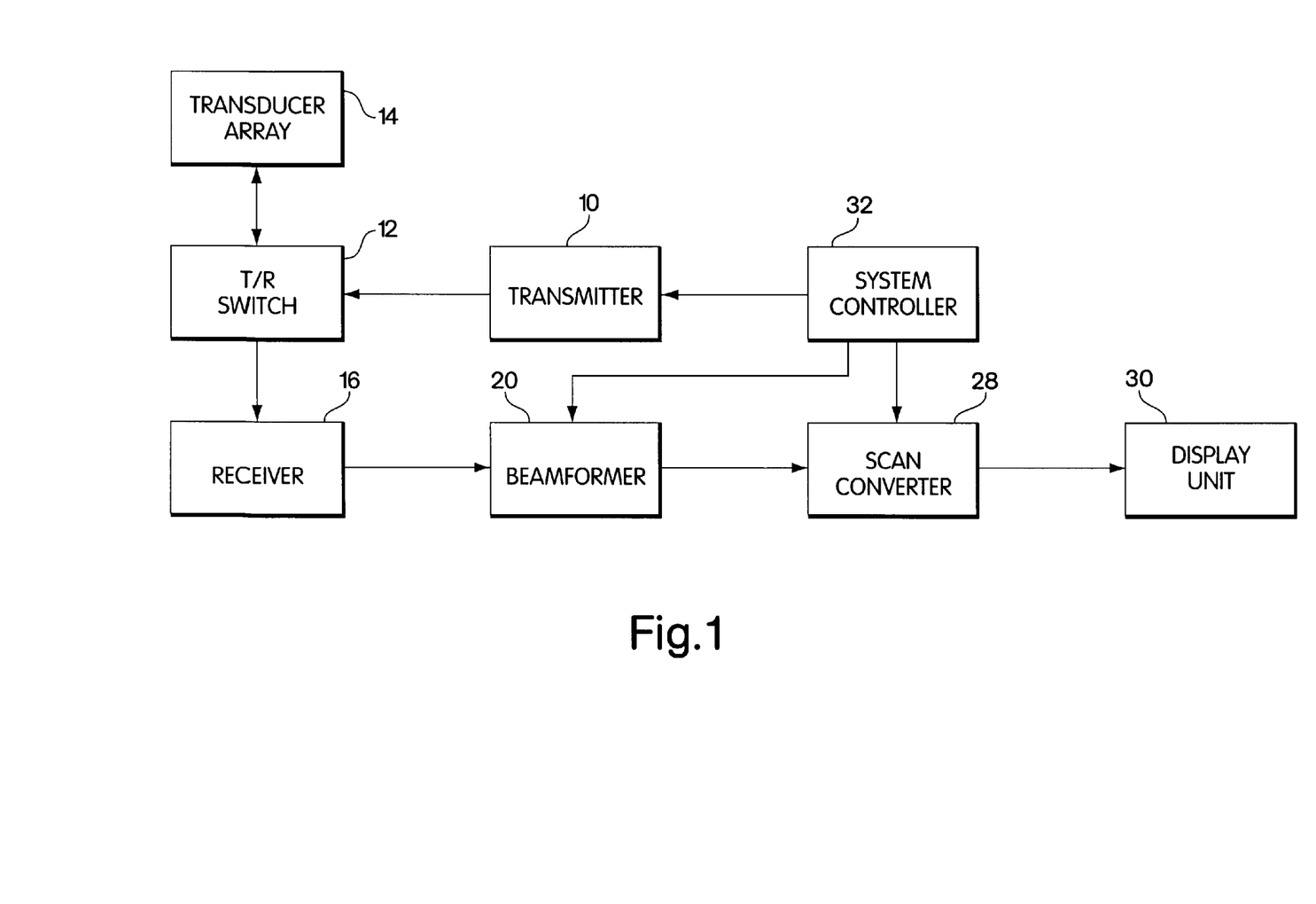
FIG. 1 is a block diagram of an example of an ultrasound imaging system.

A simplified block diagram of an example of an ultrasound imaging system is shown in FIG. 1. A transmitter 10 is coupled through a transmit/receive (T/R) switch 12, having one switch element for each transducer element, to a transducer array 14. The transducer array transmits ultrasound energy into a region of interest in a patient's body and receives reflected ultrasound energy, or echoes, from various structures and organs within the patient's body. The transducer array 14 includes an array of transducer elements. As is known in the art, by appropriately delaying the pulses applied to each transducer element by transmitter 10, a focused ultrasound beam is transmitted along a desired scan line. The transducer array 14 is configured as descried in detail below to permit three-dimensional ultrasound imaging.

The transducer array 14 is coupled through T/R switch 12 to an ultrasound receiver 16. Ultrasound energy from a given point within the patient's body is received by the transducer elements at different times. The transducer elements convert the received ultrasound energy to transducer signals which are amplified by receiver 16 and are supplied to a receive beamformer 20. The signals from each transducer element are individually delayed and then are summed by the beamformer 20 to provide a beamformer signal that represents the received ultrasound level along a desired scan line. As known in the art, the delays applied to the transducer signals may be varied during reception of ultrasound energy to effect dynamic focusing. The process is repeated for multiple scan lines to provide signals for generating an image of a region of interest in the patient's body.

In an alternative system configuration, different transducer elements are used for transmit and receive. In that configuration, the T/R switch 12 is not required, and the transmitter 10 and the receiver 16 are connected directly to the respective transmit and receive transducer elements.

A scan converter 28 converts beamformer signals generated by beamformer 20 to conventional raster display signals. The output of scan converter 28 is supplied to a video display unit 30, which displays an image of the region of interest in the patient's body. A system controller 32 provides overall control of the system. The system controller 32 performs timing and control functions and typically includes a microprocessor and associated memory.

Figure 2:
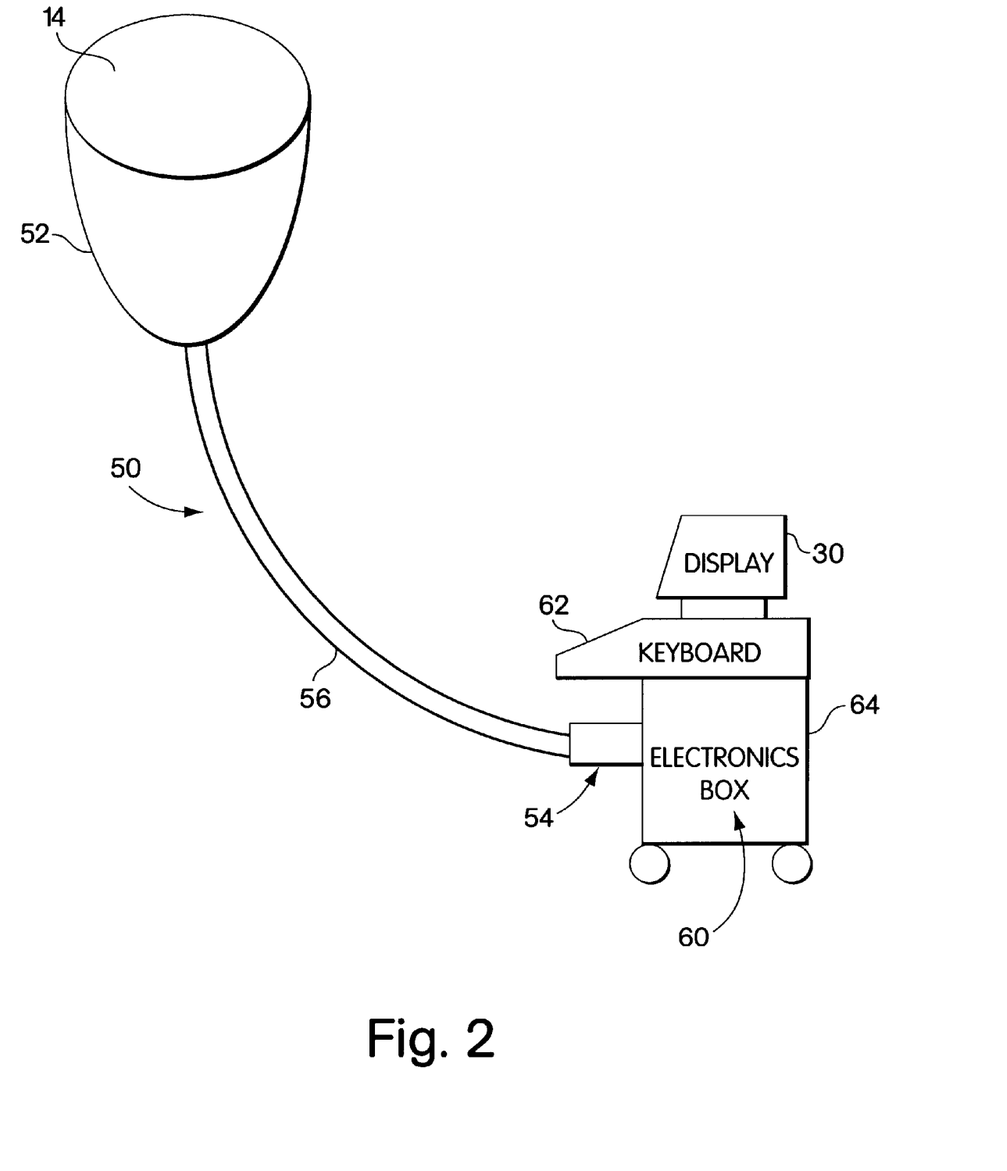
FIG. 2 is a pictorial view of an example of an ultrasound imaging system.

A pictorial view of an example of an ultrasound imaging system incorporating the present invention is shown in FIG. 2. A transducer assembly 50 (not shown to scale) includes a transducer handle, or head 52, a transducer connector 54 and a cable 56 interconnecting handle 52 and connector 54. The transducer assembly 50 is attached by connector 54 to an electronics console 60, which may include display unit 30, a keyboard 62 and an electronics box 64. As described below, the transducer handle 52 includes an ultrasound transducer array and may include electronic circuitry.

Figure 3:
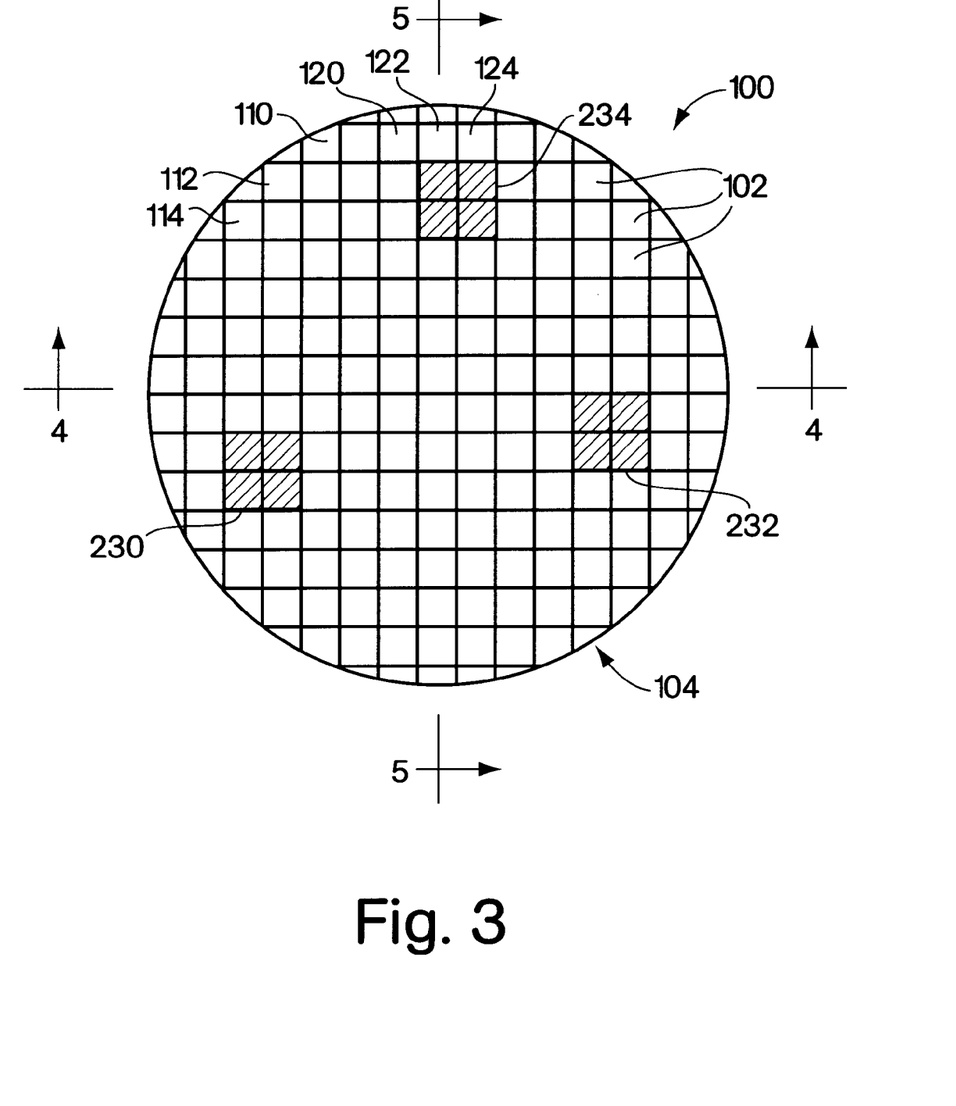
FIG. 3 is a front view of an example of an ultrasound transducer assembly in accordance with the invention.
Figure 4:
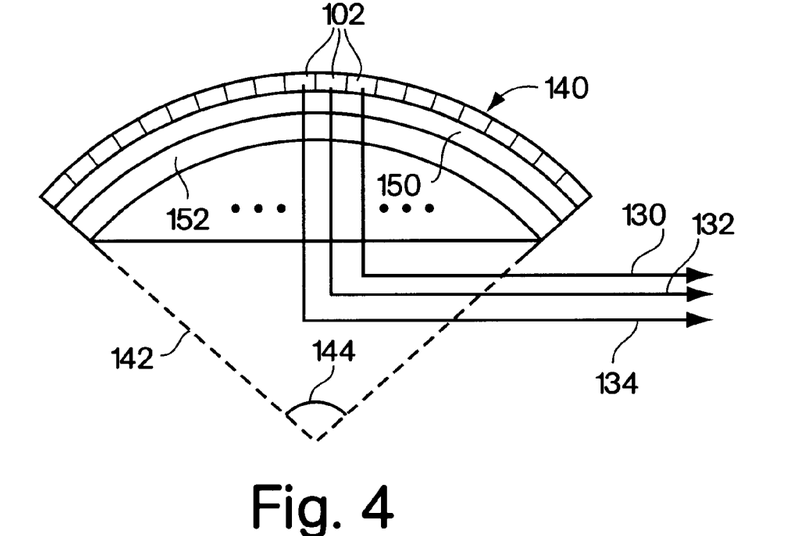
FIG. 4 is a cross-sectional view of the ultrasound transducer assembly, taken along the line 4—4 of FIG. 3.
Figure 5:
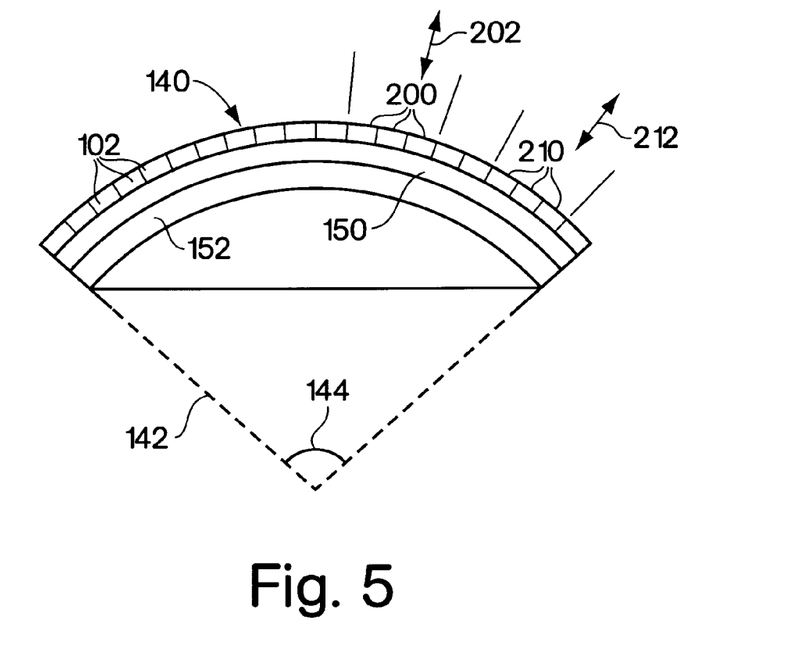
FIG. 5 is a cross-sectional view of the ultrasound transducer assembly, taken along the line 5—5 of FIG. 3.

An example of an ultrasound transducer assembly in accordance with the invention is shown in FIGS. 3–5, where like elements have the same reference numerals. A transducer assembly 100 includes a curved, two-dimensional transducer array 104 having a curved array of rows 110, 112, 114, etc. and columns 120, 122, 124, etc. of transducer elements 102. The curved array of rows and columns of transducer elements may be formed, for example, by deforming a planar array of rows and columns of transducer elements into a desired shape. A transmitting and receiving surface 140 of transducer array 104 is curved in two orthogonal directions and is non-cylindrical.

The example of FIGS. 3–5 includes a relatively small number of transducer elements 102 to illustrate the principles of the invention. A transducer assembly for high resolution imaging may include several hundred to a few thousand transducer elements.

Transducer assembly 100 further includes conductors 130, 132, 134, etc. which respectively connect each transducer element to circuitry of the ultrasound imaging system in electronics box 64. Part of the circuitry may be located in transducer handle 52 (FIG. 2) and/or in connector 54.

As indicated above, the transmitting and receiving surface 140 of transducer array 104 has a curved, two-dimensional surface contour that is non-cylindrical. In the example of FIGS. 3–5, the surface contour of the transmitting and receiving surface 140 has a spherical shape. More particularly, transmitting and receiving surface 140 is a portion of a spherical surface. Although the term "spherical" is used to describe the shape of the transmitting and receiving surface, it will be understood that transmitting and receiving surface 140 is a portion of a spherical surface. In the example of a spherical array, surface 140 may be defined by a radius of curvature 142 and a field of view angle 144. The radius of curvature 142 may be in a range of about 5 millimeters (mm) to 1 meter, and is typically in a range of about 10 mm to 60 mm, but is not limited to these ranges. The field of view angle 144 may be in a range of about 1 degree to 300 degrees, and is typically in a range of about 50 degrees to 150 degrees, but is not limited to these ranges. A relatively large radius of curvature may be utilized in a transducer assembly configured for external use, whereas a relatively small radius of curvature and a large angle may be utilized in a transducer assembly mounted on an invasive probe or otherwise intended for internal use.

Transducer array 104 is further defined by the peripheral shape of the transmitting and receiving surface. In the example of FIG. 3, the transmitting and receiving surface has a circular peripheral shape. It will be understood that the periphery of the transmitting and receiving surface may have any desired shape, such as square, rectangular, elliptical or any other regular or irregular shape.

Transducer array 104 is further defined by transducer elements 102. More particularly, the sizes of the transducer elements and the spacings between transducer elements depend on the transducer frequency and the desired image resolution. Because the transducer assembly has a curved, non-cylindrical surface contour, such as spherical, the center-to-center transducer element spacing can be greater for a given resolution than in the case of a planar array. Whereas a planar array may require a one-half $\lambda$ transducer element spacing, where $\lambda$ is the ultrasound wavelength, for a given resolution and steering angle, transducer array 104 may obtain the same viewing angle and resolution with a typical transducer element center-to-center spacing of 1.1 $\lambda$ to 1.7 $\lambda$. The increased transducer element size and spacing as compared with prior art transducer assemblies provides a number of advantages, as discussed below.

Transducer array 104 may be fabricated in a number of different ways within the scope of the present invention. The fabrication of planar, twodimensional ultrasound transducer arrays is known in the art and is described, for example, in U.S. Pat. No. 5,267,221, issued Nov. 30, 1993, to Miller et al, which is hereby incorporated by reference. In one example of a suitable fabrication technique, transducer elements 102 are formed on a planar flexible substrate, such as a backing material 150 (FIGS. 4 and 5). The substrate is then deformed to contact a form 152 having the desired transducer array shape. An adhesive material is applied to the back surface of substrate 150 so that the transducer array is affixed to form 152. Transducer array 104 may be fabricated as a single array of transducer elements or may be fabricated as a plurality of tiles affixed to the surface of form 152. Each tile may comprise a curved array of rows and columns of transducer elements. The tiles may be abutting or non-abutting, depending on the application of the transducer assembly. The tiles may have any shape and are not necessarily the same size. Furthermore, the transducer elements of the array may have any shape or size and may be uniformly or non-uniformly distributed over the transmitting and receiving surface. The transducer elements may, for example, be square, rectangular, triangular or hexagonal. Another construction may utilize a composite piezoelectric material formed to the desired surface contour.

The transmitting and receiving surface 140 of transducer array 104 shown in FIGS. 3–5 is a portion of a spherical surface. However, the present invention is not limited to transducer arrays having a spherical transmitting and receiving surface. In general, the transmitting and receiving surface 104 is curved in two orthogonal directions and is non-cylindrical. Transmitting and receiving surface 104 is defined by a curved, two-dimensional array of rows and columns of transducer elements 102. The transmitting and receiving surface 104 may have a radius of curvature that is constant or that varies over the surface. For example, the transducer array may have a larger radius of curvature near its center and a smaller radius of curvature near its periphery. The transmitting and receiving surface 104 may, for example, be a portion of a spheroid or an ellipsoid. The transmitting and receiving surface 104 may be defined by rotating a curve about an axis of revolution, thus defining a surface of revolution. The transmitting and receiving surface 104 may, for example, be dome shaped.

Both convex and concave transmitting and receiving surfaces are included within the scope of the present invention. The convex surface, as shown in FIGS. 3–5, permits a relatively wide field of view to be imaged for a given transducer size, as described below. A concave surface, may be utilized, for example, for 3D imaging through a relatively small aperture, known as keyhole imaging.

Figure 6:
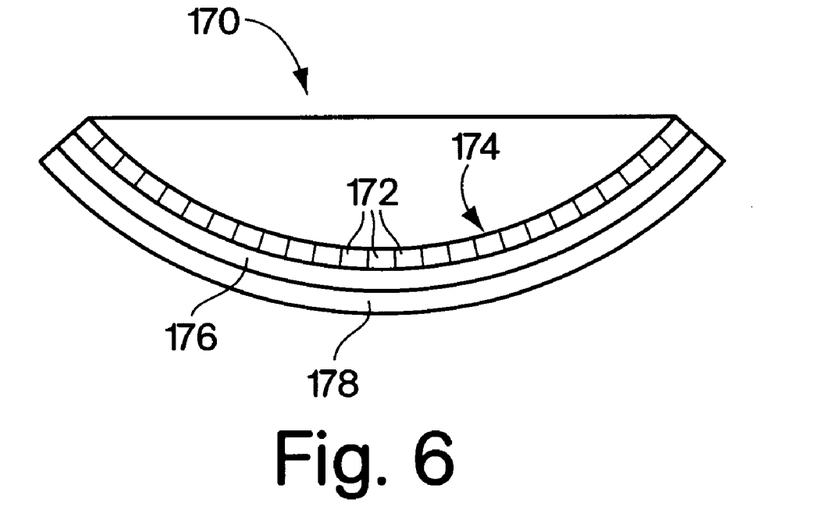
FIG. 6 is a cross-sectional view of an example of a concave ultrasound transducer assembly in accordance with the invention.

An example of a concave transducer array 170 including a curved, two-dimensional array of transducer elements 172 is shown in FIG. 6. The transmitting and receiving surface 174 of transducer array 170 may have surface contour that is concave, such as, for example, a portion of a spherical surface. Transducer elements 172 may be formed on a flexible substrate 176 which is affixed to a form 178 having a concave shape. Concave transmitting and receiving surface 174 is curved in two orthogonal directions and is non-cylindrical as described above.

Figure 7:
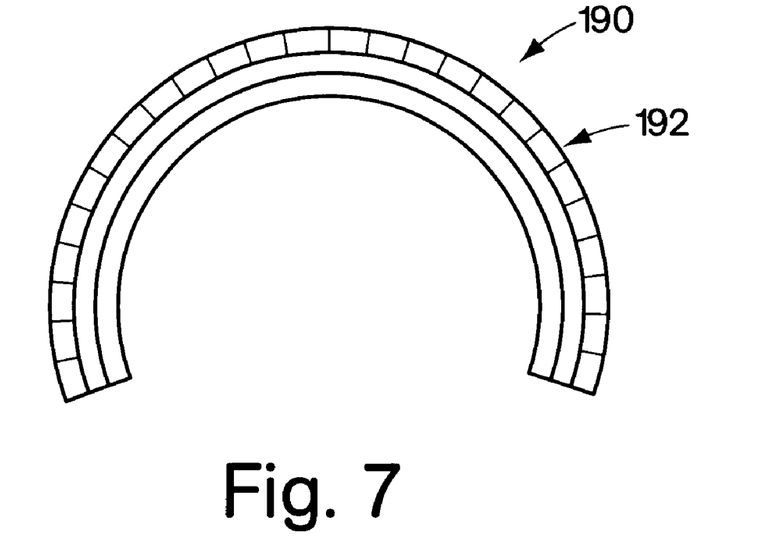
FIG. 7 is a cross-sectional view of another embodiment of an ultrasound transducer assembly in accordance with the invention.

An example of a spherical transducer array 190 having a transmitting and receiving surface 192 with a field of view angle greater than 180° is shown in FIG. 7. A transducer assembly of this shape typically has a relatively small radius of curvature and, as noted above, may be utilized at the distal end of an invasive probe for imaging of a body cavity.

The transducer assembly of the present invention may be utilized for three-dimensional imaging of an image volume of interest in a patient's body. The transducer elements of the transducer array are connected to the channels of an ultrasound imaging system, either directly or through subarray beamformers or switches. As noted above, the ultrasound imaging system includes a transmit beamformer for steering and focusing of transmitted ultrasound energy, and a receive beamformer for steering and focusing of received ultrasound echoes. The transducer assembly of the present invention, to a large degree, eliminates the need for beam steering, since different transducer elements of the array face different directions.

As shown in FIG. 5, transducer elements 200 of array 104 may be utilized for transmitting and receiving in a direction 202, and transducer elements 210 may be utilized for transmitting and receiving ultrasound energy in a direction 212. The region of the transducer array that is utilized for transmitting and receiving ultrasound energy is conventionally known as the active aperture. With reference to FIG. 3, apertures 230, 232 and 234, which may be active at different times, point in different directions, even in the absence of beam steering, because of the spherical surface contour of transducer array 104. The active aperture may be defined and stepped to different locations on transducer array 104 by electronically activating different channels of the transmit and receive beamformers connected to transducer array 104.

By acquiring data from multiple apertures that cover all or a selected part of the transmitting and receiving surface, a three-dimensional volume can be imaged. The three-dimensional image data may be acquired with little or no beam steering. The transmit and receive beams may be focused by applying appropriate delays to the transmitted and received signals of transducer elements in the active aperture.

Figure 8:
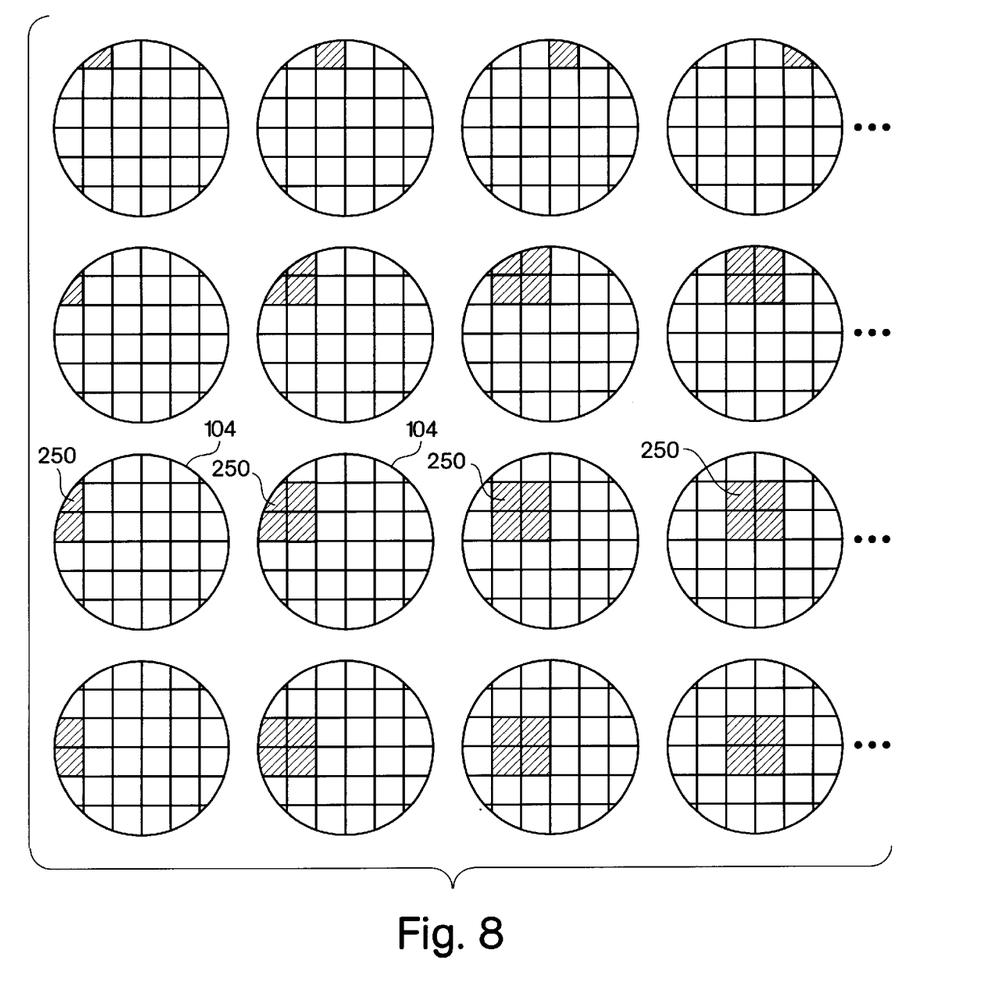
FIG. 8 shows front views of an ultrasound transducer assembly, illustrating an example of a three-dimensional imaging sequence.

An example of a suitable imaging sequence for three-dimensional imaging utilizing the ultrasound transducer assembly of the invention is shown in FIG. 8. It will be understood that a transducer array suitable for high resolution imaging would have many more transducer elements than the one shown for illustrative purposes in FIG. 8. An active aperture 250 containing a selected number of transducer elements is stepped across the transducer array 104.

The active aperture 250 includes a selected number of rows and columns of transducer elements. Near the edges of transducer array 104, the number of transducer elements in active aperture 250 may be reduced. An imaging sequence may involve stepping across successive lines of an imaging pattern until image data for a desired image volume has been acquired. Different active apertures may or may not overlap. The imaging pattern may be regular, as shown in FIG. 8, may be random or may be interleaved. Transducer elements of the active aperture do not necessarily abut against each other. The size of the active aperture may vary during the imaging sequence. The image data acquired with each active aperture is combined to form a three-dimensional image of the image volume.

The transducer array of the present invention, illustrated by way of example in FIGS. 3–5 as a spherical array, has a number of advantages in comparison with prior art approaches to three-dimensional ultrasound imaging. The transducer array of the invention does not require transducer elements having dimensions of one-half λ in order to obtain high resolution images. Instead, transducer elements with dimensions and center-to-center spacings of 1.1 λ to 1.7 λ provide resolution that is comparable to that obtained with one-half λ elements in a planar array. Thus, the number of transducer elements in the array may be reduced. For example, a spherical transducer array having 32×32 elements may provide image quality that is comparable to the image quality of a planar array having 64×64 elements. Thus, the number of transducer elements may be reduced by a factor of four. It will be understood that the transducer elements utilized in the array of the present invention are not limited to dimensions and center-to-center spacings of 1.1 λ to 1.7 λ, but may be larger or smaller, depending on the application.

Because the transducer element pitch is coarser, fabrication of the array is easier, thereby lowering risk and cost. The elements are easier to fabricate because they can be supported during dicing.

The number of elements used to acquire image data can be varied from a maximum at the center of the image to a minimum at the edges. This provides the best image quality at the center, where it is needed most. Also, because the transducer element pitch is coarser than in prior art approaches, higher frequency transducers may be utilized.

The transducer array of the present invention can utilize large transmit and receive apertures without adding large numbers of elements. This is especially helpful in obstetric and abdominal imaging.

The transducer array of the present invention does not require large system delays because the transducer elements are pointing in approximately the desired direction. Furthermore, the directional pattern of the transducer elements is less critical than with the planar two-dimensional array, because the transducer elements are pointing in approximately the desired direction.

The transducer element count may be low enough to permit use of a multiplexer only addressing scheme. In some applications, the element count may be low enough to permit use of one wire per transducer element connected to the imaging system without producing an excessively bulky and inflexible cable, so that complex electronics are not required in the transducer handle. In some instances, the transducer elements may be large enough to not require preamplifiers. In other applications, the transducer elements may be connected to subarray beamforming circuitry located in the transducer handle, as described, for example, in U.S. Pat. No. 5,229,933, issued Jul. 20, 1993 to Larson, III, to reduce the required number of conductors in the transducer cable.

While there have been shown and described what are at present considered the preferred embodiments of the present invention, it will be obvious to those skilled in the art that various changes and modifications may be made therein without departing from the scope of the invention as defined by the appended claims.

What is claimed is:

1. An ultrasound system, comprising:

an ultrasound transducer assembly including an array of ultrasound transducer elements having a two-dimensional transmitting and receiving surface curved in at least two orthogonal directions; and a control circuit that enables an aperture to be swept across the array in a two-dimensional pattern to produce three-dimensional data.

2. An ultrasound system as defined in claim 1 wherein said array comprises a curved, two-dimensional array of rows and columns of said transducer elements.

3. An ultrasound system as defined in claim 2 wherein said transmitting and receiving surface comprises a portion of a spherical surface.

4. An ultrasound system as defined in claim 3 wherein said spherical surface has a radius in a range of 5 millimeters to 1 meter.

5. An ultrasound system as defined in claim 3 wherein said array has a field of view angle in a range of 1 degree to 300 degrees.

6. An ultrasound system as defined in claim 1 wherein said transmitting and receiving surface is convex.

7. An ultrasound system as defined in claim 1 wherein said transmitting and receiving surface is concave.

8. An ultrasound system as defined in claim 1 wherein said array comprises a flexible substrate containing said transducer elements affixed to a form that defines said transmitting and receiving surface.

9. An ultrasound system as defined in claim 8 wherein said flexible substrate comprises a piezoelectric material affixed to a backing material.

10. An ultrasound system as defined in claim 8 wherein said substrate comprises a composite piezoelectric material.

11. An ultrasound system as defined in claim 1 wherein said array comprises a plurality of tiles affixed to a form that defines said transmitting and receiving surface, each of said tiles comprising a curved, two-dimensional array of rows and columns of said transducer elements.

12. An ultrasound system as defined in claim 1 wherein said transmitting and receiving surface comprises a portion of an ellipsoid.

13. An ultrasound system as defined in claim 1 wherein said transmitting and receiving surface comprises a portion of a spheroid.

14. An ultrasound system as defined in claim 1 wherein said transmitting and receiving surface comprises a surface of revolution that is defined by rotating a curve about an axis of revolution.

15. An ultrasound system as defined in claim 1 wherein said transmitting and receiving surface is dome-shaped.

16. A phased array ultrasound imaging system comprising:

an array of ultrasound transducer elements having a two-dimensional transmitting and receiving surface that is curved in at least two orthogonal directions;

a transmit beamformer coupled to said transducer array for controlling transmission of ultrasound energy with said transducer array into a region of interest in a patient's body by sweeping an aperture across the array in a two-dimensional pattern;

a receive beamformer coupled to said transducer array for processing received signals representative of received ultrasound echoes to form at least one receive beam and to generate 3-D image data representative of the ultrasound echoes in said receive beam; and a display assembly responsive to said image data for displaying an ultrasound image of the region of interest.

17. A phased array ultrasound imaging system as defined in claim 16 wherein said array comprises a curved, two-dimensional array of rows and columns of said transducer elements.

18. A phased array ultrasound imaging system as defined in claim 17 wherein said transmitting and receiving surface comprises a portion of a spherical surface.

19. A phased array ultrasound imaging system as defined in claim 16 wherein said transmitting and receiving surface is convex.

20. A phased array ultrasound imaging system as defined in claim 16 wherein said transmitting and receiving surface is concave.

21. A phased array ultrasound imaging system as defined in claim 16 wherein said transmit beamformer and said receive beamformer comprise means for transmitting and receiving, respectively, with different subsets of said transducer elements for generating a three-dimensional image of the region of interest.

22. A phased array ultrasound imaging system as defined in claim 16 wherein said transmitting and receiving surface comprises a portion of an ellipsoid.

23. A phased array ultrasound imaging system as defined in claim 16 wherein said transmitting and receiving surface comprises a portion of a spheroid.

24. A phased array ultrasound imaging system as defined in claim 16 wherein said transmit beamformer comprises means for transmitting ultrasound energy with different active apertures on said array, said receive beamformer comprises means for forming receive beams and generating image data corresponding to each of said active apertures, wherein said image data represents a three-dimensional image volume.

25. An ultrasound system comprising:

a transducer handle containing an array of ultrasound transducer elements having a two-dimensional transmitting and receiving surface that is curved in at least two orthogonal directions;

a transducer connector for connecting the transducer assembly to an electronics unit of the ultrasound imaging system;

a transducer cable interconnecting said handle and said connector, said transducer cable including conductors for connecting said array to the electronics unit of said ultrasound imaging system; and a control circuit that enables an aperture to be swept across the array in a two-dimensional pattern to produce three-dimensional data.

* * * * *